(12) United States Patent
Trautman et al.

(10) Patent No.: US 9,421,351 B2
(45) Date of Patent: Aug. 23, 2016

(54) SELF-ACTUATING APPLICATOR FOR MICROPROJECTION ARRAY

(75) Inventors: Joseph C. Trautman, Sunnyvale, CA (US); Lorin Olson, Scotts Valley, CA (US)

(73) Assignee: ALZA CORPORATION, Mountain View, CA (US)

( * ) Notice: Subject to any disclaimer, the term of this patent is extended or adjusted under 35 U.S.C. 154(b) by 1053 days.

(21) Appl. No.: 11/477,045

(22) Filed: Jun. 27, 2006

(65) Prior Publication Data

US 2007/0027427 A1 Feb. 1, 2007

Related U.S. Application Data

(63) Continuation of application No. 10/971,871, filed on Oct. 21, 2004, now Pat. No. 7,097,631.

(60) Provisional application No. 60/516,182, filed on Oct. 31, 2003.

(51) Int. Cl.
*A61M 37/00* (2006.01)
*A61B 17/20* (2006.01)
*A61B 17/92* (2006.01)

(52) U.S. Cl.
CPC ........ *A61M 37/0015* (2013.01); *A61B 17/205* (2013.01); *A61B 2017/925* (2013.01); *A61M 2037/0023* (2013.01); *A61M 2037/0038* (2013.01); *A61M 2037/0046* (2013.01)

(58) Field of Classification Search
CPC ................ A61M 37/0015; A61M 2037/0038; A61M 2037/0046; A61M 2037/0023; A61B 17/205; A61B 2017/925

USPC .............. 604/46, 47, 20, 57, 59, 93.01, 112; 600/573, 572, 566, 567; 606/181–183, 606/185, 167
See application file for complete search history.

(56) References Cited

U.S. PATENT DOCUMENTS

| | | |
|---|---|---|
| 3,136,314 A | 6/1964 | Kravitz |
| RE25,637 E | 9/1964 | Kravitz et al. |
| 3,814,097 A | 6/1974 | Ganderton et al. |
| 3,964,482 A * | 6/1976 | Gerstel et al. ............. 604/890.1 |
| 4,109,655 A | 8/1978 | Chacomac |
| 4,453,926 A | 6/1984 | Galy |
| 4,527,561 A | 7/1985 | Burns |
| 5,250,023 A | 10/1993 | Lee et al. |

(Continued)

FOREIGN PATENT DOCUMENTS

| | | |
|---|---|---|
| GB | 2 064 329 A | 6/1981 |
| WO | WO 93/17754 | 9/1993 |

(Continued)

OTHER PUBLICATIONS

U.S. Appl. No. 10/674,626.

(Continued)

*Primary Examiner* — Bradley Osinski

(57) ABSTRACT

An applicator for applying a microprojection member to the stratum corneum of a patient having a housing, a piston moveable within the housing and a cap adapted to activate the applicator. The applicator is self-setting and auto-triggering, which allows the applicator to be used by patient's having neither the strength, nor the manual dexterity to pre-set and activate other types of applicator devices.

22 Claims, 8 Drawing Sheets

(56) References Cited

U.S. PATENT DOCUMENTS

| | | | |
|---|---|---|---|
| 5,279,544 A | 1/1994 | Gross et al. | |
| 5,350,392 A * | 9/1994 | Purcell et al. | 606/182 |
| 5,439,473 A | 8/1995 | Jorgensen | |
| 5,487,726 A | 1/1996 | Rabenau et al. | |
| 5,827,297 A * | 10/1998 | Boudjema | 606/133 |
| 5,879,326 A | 3/1999 | Godshall et al. | |
| 5,964,718 A | 10/1999 | Duchon et al. | |
| 6,050,988 A | 4/2000 | Zuck | |
| 6,083,196 A | 7/2000 | Trautman et al. | |
| 6,230,051 B1 | 5/2001 | Cormier et al. | |
| 6,248,120 B1 | 6/2001 | Wyszogrodzki | |
| 6,322,808 B1 | 11/2001 | Trautman et al. | |
| 6,533,949 B1 * | 3/2003 | Yeshurun et al. | 216/11 |
| 6,537,242 B1 * | 3/2003 | Palmer | 604/22 |
| 6,835,184 B1 * | 12/2004 | Sage et al. | 604/46 |
| 6,855,131 B2 | 2/2005 | Trautman et al. | |
| 6,855,372 B2 | 2/2005 | Trautman et al. | |
| 6,918,901 B1 | 7/2005 | Theeuwes et al. | |
| 6,953,589 B1 | 10/2005 | Trautman et al. | |
| 7,097,631 B2 | 8/2006 | Trautman et al. | |
| 7,131,960 B2 | 11/2006 | Trautman et al. | |
| 7,184,826 B2 | 2/2007 | Cormier et al. | |
| 7,588,552 B2 * | 9/2009 | Yeshurun et al. | 604/22 |
| 2002/0091357 A1 | 7/2002 | Trautman et al. | |
| 2002/0123675 A1 | 9/2002 | Trautman et al. | |
| 2002/0128599 A1 * | 9/2002 | Cormier et al. | 604/116 |
| 2002/0177839 A1 | 11/2002 | Cormier et al. | |
| 2003/0083645 A1 | 5/2003 | Angel et al. | |
| 2003/0181936 A1 | 9/2003 | Trautman et al. | |
| 2003/0199810 A1 | 10/2003 | Trautman et al. | |
| 2003/0208167 A1 | 11/2003 | Prausnitz et al. | |
| 2004/0062813 A1 | 4/2004 | Cormier et al. | |
| 2004/0087893 A1 * | 5/2004 | Kwon | 604/46 |
| 2004/0138610 A1 | 7/2004 | Cormier et al. | |
| 2004/0236271 A1 | 11/2004 | Theeuwes et al. | |
| 2004/0265354 A1 | 12/2004 | Ameri et al. | |
| 2005/0084604 A1 | 4/2005 | Trautman et al. | |
| 2005/0106209 A1 | 5/2005 | Ameri et al. | |
| 2005/0106227 A1 | 5/2005 | Zalipsky et al. | |
| 2005/0123507 A1 | 6/2005 | Ameri et al. | |
| 2005/0137531 A1 | 6/2005 | Prausnitz et al. | |
| 2005/0148926 A1 | 7/2005 | Trautman et al. | |
| 2005/0165358 A1 | 7/2005 | Yeshurun et al. | |
| 2005/0234401 A1 | 10/2005 | Trautman et al. | |
| 2005/0256045 A1 | 11/2005 | Ameri | |
| 2005/0261631 A1 * | 11/2005 | Clarke et al. | 604/173 |
| 2006/0095061 A1 | 5/2006 | Trautman et al. | |
| 2006/0142691 A1 | 6/2006 | Cormier et al. | |
| 2006/0177494 A1 | 8/2006 | Cormier et al. | |
| 2006/0188555 A1 | 8/2006 | Cormier et al. | |
| 2006/0200069 A1 | 9/2006 | Cormier et al. | |
| 2006/0204562 A1 | 9/2006 | Cormier et al. | |
| 2006/0275170 A1 | 12/2006 | Ameri et al. | |
| 2007/0009587 A1 | 1/2007 | Daddona et al. | |

FOREIGN PATENT DOCUMENTS

| | | |
|---|---|---|
| WO | WO 96/17648 | 6/1996 |
| WO | WO 96/37155 | 11/1996 |
| WO | WO 96/37256 | 11/1996 |
| WO | WO 97/03718 | 2/1997 |
| WO | WO 97/42886 | 11/1997 |
| WO | WO 97/48440 | 12/1997 |
| WO | WO 97/48441 | 12/1997 |
| WO | WO 97/48442 | 12/1997 |
| WO | WO 98/00193 | 1/1998 |
| WO | WO 98/11937 | 3/1998 |
| WO | WO 98/28037 | 7/1998 |
| WO | WO 98/29298 | 7/1998 |
| WO | WO 98/29365 A1 | 7/1998 |
| WO | WO 99/26539 | 6/1999 |
| WO | WO 99/29364 | 6/1999 |
| WO | WO 99/64580 | 12/1999 |
| WO | 02/30301 A1 | 4/2002 |

OTHER PUBLICATIONS

U.S. Appl. No. 10/045,842.
U.S. Appl. No. 09/976,763.
U.S. Appl. No. 60/514,433.
U.S. Appl. No. 60/514,387.

* cited by examiner

SELF-ACTUATING APPLICATOR FOR MICROPROJECTION ARRAY

CROSS-REFERENCE TO RELATED APPLICATIONS

This application is a continuation of U.S. application Ser. No. 10/971,871, filed Oct. 21, 2004, now U.S. Pat. No. 7,097,631 which claims the benefit of U.S. Provisional Application No. 60/516,182 filed Oct. 31, 2003.

FIELD OF THE PRESENT INVENTION

The present invention relates to an apparatus and method for applying a penetrating member to the skin by impact, and more particularly, the invention relates to a self-setting, auto-trigging impact device to reproducibly penetrate the stratum corneum with a penetrating member, such as a microprotrusion array, for transdermal delivery or sampling of an agent.

BACKGROUND OF THE INVENTION

Active agents (or drugs) are most conventionally administered either orally or by injection. Unfortunately, many agents are completely ineffective or have radically reduced efficacy when orally administered since they either are not absorbed or are adversely affected before entering the bloodstream and thus do not possess the desired activity. Further, orally administered agents typically do not take effect as quickly as injected agents. On the other hand, the direct injection of the agent into the bloodstream, while assuring no modification of the agent during administration, is a difficult, inconvenient, painful and uncomfortable procedure which sometimes results in poor patient compliance.

Hence, in principle, transdermal delivery provides for a method of administering active agents that would otherwise need to be delivered via hypodermic injection or intravenous infusion. Transdermal agent delivery offers improvements in both of these areas. Transdermal delivery, when compared to oral delivery, avoids the harsh environment of the digestive tract, bypasses gastrointestinal drug metabolism, reduces first-pass effects and avoids the possible deactivation by digestive and liver enzymes.

The word "transdermal", as used herein, refers to delivery of an active agent (e.g., a therapeutic agent, such as a drug or an immunologically active agent, such as a vaccine) through the skin to the local tissue or systemic circulatory system without substantial cutting or penetration of the skin, such as cutting with a surgical knife or piercing the skin with a hypodermic needle.

Transdermal agent delivery systems generally rely on passive diffusion to administer the agent, while active transdermal agent delivery systems rely on an external energy source, including electricity (e.g., iontophoresis) and ultrasound (e.g., phonophoresis), to deliver the agent. Passive transdermal agent delivery systems, which are more common, typically include an agent reservoir containing a high concentration of the agent. The reservoir is adapted to contact the skin, which enables the agent to diffuse through the skin and into the body tissues or bloodstream of a patient.

As is well known in the art, transdermal agent flux is dependent upon the condition of the skin, the size and physical/chemical properties of the agent molecule, and the concentration gradient across the skin. Because of the low permeability of the skin to many active agents, transdermal delivery has had limited applications. This low permeability is attributed primarily to the stratum corneum, the outermost skin layer, which consists of flat, dead cells filled with keratin fibers (i.e., keratinocytes) surrounded by lipid bilayers. This highly-ordered structure of the lipid bilayers confers a relatively impermeable character to the stratum corneum.

One common method of increasing the passive transdermal diffusional agent flux involves pre-treating the skin with, or co-delivering with the drug, a skin permeation enhancer. A permeation enhancer, when applied to a body surface through which the agent is delivered, enhances the flux of the agent therethrough. However, the efficacy of these methods in enhancing transdermal protein flux has, in several instances, been limited.

As stated, active transport systems use an external energy source to assist and, in most instances, enhance agent flux through the stratum corneum. One such enhancement for transdermal agent delivery is referred to as "electrotransport." Electrotransport uses an electrical potential, which results in the application of electric current to aid in the transport of the agent through a body surface, such as skin.

There also have been many techniques and systems developed to mechanically penetrate or disrupt the outermost skin layers thereby creating pathways into the skin in order to enhance the amount of agent being transdermally delivered. Early vaccination devices, known as scarifiers, generally included a plurality of tines or needles that were applied to the skin to and scratch or make small cuts in the area of application. The vaccine was applied either topically on the skin, such as disclosed in U.S. Pat. No. 5,487,726, or as a wetted liquid applied to the scarifier tines, such as disclosed in U.S. Pat. Nos. 4,453,926, 4,109,655, and 3,136,314.

There are, however, numerous disadvantages and drawbacks associated with scarifiers. A serious disadvantage in using a scarifier to deliver an agent is the difficulty in determining the transdermal agent flux and the resulting dosage delivered. Also, due to the elastic, deforming and resilient nature of skin to deflect and resist puncturing, the tiny piercing elements often do not uniformly penetrate the skin and/or are wiped free of a liquid coating of an agent upon skin penetration.

Additionally, due to the self-healing process of the skin, the punctures or slits made in the skin tend to close up after removal of the piercing elements from the stratum corneum. Thus, the elastic nature of the skin acts to remove the active agent liquid coating that has been applied to the tiny piercing elements upon penetration of these elements into the skin. Furthermore, the tiny slits formed by the piercing elements heal quickly after removal of the device, thus limiting the passage of the liquid agent solution through the passageways created by the piercing elements and in turn limiting the transdermal flux of such devices.

Other systems and apparatus that employ tiny skin piercing elements to enhance transdermal drug delivery are disclosed in U.S. Pat. Nos. 5,879,326, 3,814,097, 5,279,54, 5,250,023, 3,964,482, Reissue No. 25,637, and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365; all incorporated herein by reference in their entirety.

The disclosed systems and apparatus employ piercing elements of various shapes, sizes and arrays to pierce the outermost layer (i.e., the stratum corneum) of the skin. The piercing elements disclosed in these references generally extend perpendicularly from a thin, flat member, such as a pad or sheet. The piercing elements in some of these devices are extremely small, some having a microprojection length of only about 25-400 microns and a microprojection thickness of only about 5-50 microns. These tiny piercing/cutting elements make correspondingly small microslits/microcuts in the stratum corneum for enhancing transdermal agent delivery therethrough.

The disclosed systems typically include a reservoir for holding the active agent and a delivery system that is adapted to transfer the agent from the reservoir through the stratum corneum, such as by hollow tines of the device itself. Illustrative is the device disclosed in PCT Pub. WO 93/17754, which has a liquid agent reservoir.

As disclosed in U.S. patent application Ser. No. 10/045, 842, which is fully incorporated by reference herein, it is also possible to have the active agent that is to be delivered coated on the microprojections or microprojection array instead of contained in a physical reservoir. This eliminates the necessity of a separate physical reservoir and developing a agent formulation or composition specifically for the reservoir. The skin piercing microprotrusions have a dry coating of the pharmacologically active agent. Delivery of the agent is facilitated when the microprotrusions pierce the skin of a patient and the patient's interstitial fluid contacts and dissolves the active agent.

When microprojection arrays are used to improve delivery or sampling of agent through the skin, consistent, complete, and repeatable penetration is desired. Manual application of a skin patch, having microprojections protruding from its skin-contacting side, often results in significant variation in puncture depth across the length and width of the patch. In addition, manual application results in large variations in puncture depth between applications due to the manner in which the user applies the array a microprojection array to the stratum corneum with an automatic device, which provides in a consistent and repeatable manner, stratum corneum piercing, not only over the length and width of the microprotrusion array, but also from application of one microprojection array to the next.

Some known spring loaded applicator devices for delivery of lancets for body fluid (e.g., blood) sampling are described in PCT Pub. No. WO 99/26539 and WO 97/42886. However, these devices are difficult to use because they require two-handed pre-setting of the applicator device prior to the application. In particular, the known spring loaded lancet applicators require either two sections of the device to be pulled apart for pre-setting or require one part of the device to be pulled apart for pre-setting or require one part of the device to be twisted with respect to another part of the device for pre-setting. In both of these motions, a two-handed pre-setting operation is required. Many of the patients using these devices possess neither the strength, nor the manual dexterity to pre-set these known applicator devices.

In U.S. application Ser. No. 09/976,763 a further spring loaded applicator, which is adapted to apply a microprojection array, is disclosed. The noted applicator includes a pre-setting mechanism that allows one-handed pre-setting of the applicator.

A drawback of the applicator is thus that the applicator still requires a separate step of manually pre-setting the device prior to use. It would thus be desirable to provide an applicator that is eliminates the step of manually pre-setting the applicator prior to use.

It is therefore an object of the present invention to provide an applicator for applying a microprojection member or array to a patient that substantially reduces or eliminates the aforementioned drawbacks and disadvantages associated with prior art applicator devices.

It is another object of the present invention to provide an auto pre-setting applicator that eliminates the step of manually pre-setting the applicator prior to use.

It is another object of the present invention to provide an auto pre-setting and auto triggering applicator that is adapted to apply a microprojection member or array to a patient.

It is another object of the present invention to provide an auto pre-setting and auto triggering applicator that applies microprojection arrays in a consistent and repeatable manner.

It is another object of the present invention to provide an auto pre-setting and auto triggering for applying a microprojection array that is compact in design.

It is another object of the present invention to provide an auto pre-setting and auto triggering applicator for applying a microprojection array that requires minimal components and has an extended useful life.

SUMMARY OF THE INVENTION

In accordance with the above objects and those that will be mentioned and will become apparent below, the applicator for applying a microprojection array to a patient in accordance with this invention comprises (i) a housing having a first and second end; (ii) a cap that is adapted to move from a primary position to a pre-set position relative to the housing, the first end of the housing being adapted to receive the microprojection member; (iii) a piston slideably disposed within the housing for impacting the microprojection member against the stratum corneum, the piston being adapted to move from a pre-set position to an activated position in which the piston extends from the end of the housing opposite the cap; (iv) an impact spring in communication with the cap and the piston, the impact spring being adapted to provide and an impact force to the piston and bias the piston out of the first end of the housing toward an activated position proximate the stratum corneum, wherein the impact spring is energized when the cap and the piston are in the pre-set position; (v) a pre-setting spring in communication with the cap and the housing, the pre-setting spring being adapted to provide a pre-setting force to the cap and bias the cap from the pre-set position to the primary position, wherein the pre-setting spring is energized when the piston is in the activated position; (vi) a first latching assembly in communication with the cap and the piston, the first latching assembly being adapted to cooperate with the cap and the pre-setting spring to return the piston to the primary position when the cap is moved from the pre-set position to the primary position; (vii) a second latching assembly in communication with the housing and the piston to position the piston in the pre-set position; and (vii) a releasing member in communication with the cap, said releasing member being adapted to communicate with the second latching assembly when the cap is moved from the primary position to the pre-set position, wherein the impact spring is energized and the releasing member disengages, whereby the piston moves from the pre-set position to the activated position and forces the microprojection member into the stratum corneum.

Preferably, the impact spring has an impact (or stored) energy in the range of approximately 0.005-0.5 joules/cm². More preferably, the impact spring 40 has a stored energy in the range of approximately 0.01-0.3 joules/cm².

In one embodiment of the invention, the impact spring has an impact velocity in the range of approximately 0.5-20 meters(m)/sec, more preferably, in the range of approximately 1.0-10 m/sec.

In one embodiment of the invention, the piston has a surface area in range of approximately 0.1-20 cm$^2$, more preferably, in the range of 1.0-10 cm$^2$.

In a preferred embodiment of the invention, the microprojection member includes at least one biologically active agent.

In accordance with a further embodiment of the invention, the device for impacting a microprojection member against the stratum corneum of a patient comprises (i) a housing having a first and second end, the housing including a cap that is adapted to move from a primary position to a pre-set position relative to the housing; (ii) a retainer adapted to engage the housing proximate the second end, the retainer being further adapted to receive and position the microprojection member; (iii) a housing having a first and second end; (iv) a cap that is adapted to move from a primary position to a pre-set position relative to the housing, the first end of the housing being adapted to receive the microprojection member; (v) a piston slideably disposed within the housing for impacting the microprojection member against the stratum corneum, the piston being adapted to move from a pre-set position to an activated position; (vi) an impact spring in communication with the cap and the piston, the impact spring being adapted to provide and an impact force to the piston and bias the piston out of the first end of the housing toward an activated position proximate the stratum corneum, wherein the impact spring is energized when the cap and the piston are in the pre-set position; (vii) a pre-setting spring in communication with the cap and the housing, the pre-setting spring being adapted to provide a pre-setting force to the cap and bias the cap from the pre-set position to the primary position, wherein the pre-setting spring is energized when the piston is in the activated position; (viii) a first latching assembly in communication with the cap and the piston, the first latching assembly being adapted to cooperate with the cap and the pre-setting spring to return the piston to the primary position when the cap is moved from the pre-set position to the primary position; (ix) a second latching assembly in communication with the housing and the piston to position the piston in the pre-set position; and (x) a releasing member in communication with the cap, said releasing member being adapted to communicate with the second latching assembly when the cap is moved from the primary position to the pre-set position, wherein the impact spring is energized and the releasing member disengages, whereby the piston moves from the pre-set position to the activated position and forces the microprojection member into the stratum corneum.

In accordance with yet another embodiment of the invention, there is disclosed a transdermal delivery system for delivering a biologically active agent to a patient that comprises (i) a patch system, the patch system including a gel pack containing an agent formulation and a microprojection member having top and bottom surfaces, a plurality of openings that extend through the microprojection member and a plurality of stratum corneum-piercing microprojections that project from the bottom surface of the microprojection member, the microprojection member being adapted to receive the gel pack whereby the agent formulation flows through the microprojection member openings, and (ii) an applicator, the applicator including a housing having a first and second end, the first end of the housing being adapted to receive the microprojection member, a cap that is adapted to move from a primary position to a pre-set position relative to the housing, a piston slideably disposed within the housing for impacting the microprojection member against the stratum corneum, the piston being adapted to move from a pre-set position to an activated position, an impact spring in communication with the cap and the piston, the impact spring being adapted to provide and an impact force to the piston and bias the piston out of the first end of the housing toward an activated position proximate the stratum corneum, wherein the impact spring is energized when the cap and the piston are in the pre-set position, a pre-setting spring in communication with the cap and the housing, the pre-setting spring being adapted to provide a pre-setting force to the cap and bias the cap from the pre-set position to the primary position, wherein the pre-setting spring is energized when the piston is in the activated position, a first latching assembly in communication with the cap and the piston, the first latching assembly being adapted to cooperate with the cap and the pre-setting spring to return the piston to the primary position when the cap is moved from the pre-set position to the primary position, a second latching assembly in communication with the housing and the piston to position the piston in the pre-set position and a releasing member in communication with the cap, said releasing member being adapted to communicate with the second latching assembly when the cap is moved from the primary position to the pre-set position, wherein the impact spring is energized and the releasing member disengages, whereby the piston moves from the pre-set position to the activated position and forces the microprojection member into the stratum corneum.

Preferably, the applicator includes a retainer adapted to engage the applicator housing proximate the second end, the retainer being further adapted to receive and position the microprojection member.

In a preferred embodiment, the agent formulation includes at least one biologically active agent.

In one embodiment of the invention, the biologically active agent is selected from the group consisting of a leutinizing hormone releasing hormone (LHRH), LHRH analogs (such as goserelin, leuprolide, buserelin, triptorelin, gonadorelin, and napfarelin, menotropins (urofollitropin (FSH) and LH)), vasopressin, desmopressin, corticotropin (ACTH), ACTH analogs such as ACTH (1-24), calcitonin, parathyroid hormone (PTH), vasopressin, deamino [Val4, D-Arg8] arginine vasopressin, interferon alpha, interferon beta, interferon gamma, erythropoietin (EPO), granulocyte macrophage colony stimulating factor (GM-CSF), granulocyte colony stimulating factor (G-CSF), interleukin-10 (IL-10), glucagon, growth hormone release hormone (GHRH), growth hormone release factor (GHRF), insulin, insultropin, calcitonin, octreotide, endorphin, TRN, NT-36 (chemical name: N-[[(s)-4-oxo-2-azetidinyl]carbonyl]-L-histidyl-L-prolinamide), liprecin, pituitary hormones (e.g., HGH, HMG, desmopressin acetate, etc), follicle luteoids, aANF, growth factors such as growth factor releasing factor (GFRF), bMSH, GH, somatostatin, bradykinin, somatotropin, platelet-derived growth factor releasing factor, asparaginase, bleomycin sulfate, chymopapain, cholecystokinin, chorionic gonadotropin, corticotropin (ACTH), erythropoietin, epoprostenol (platelet aggregation inhibitor), glucagon, HCG, hirulog, hyaluronidase, interferon, interleukins, menotropins (urofollitropin (FSH) and LH), oxytocin, streptokinase, tissue plasminogen activator, urokinase, vasopressin, desmopressin, ANP, ANP clearance inhibitors, angiotensin II antagonists, antidiuretic hormone agonists, bradykinn antagonists, ceredase, CSI's, calcitonin gene related peptide (CGRP), enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vasopressin antagonists analogs, alpha-1 antitrypsin (recombinant), TGF-beta, fondaparinux, ardeparin, dalteparin, defibrotide, enoxaparin, hirudin, nadroparin, reviparin, tinzaparin, pentosan polysulfate, oligonucleotides and oligonucleotide derivatives, such as formivirsen, alendronic acid, clodronic acid, etidronic acid, ibandronic acid, incadronic acid, pamidronic acid, risedronic acid, tiludronic acid, zoledronic acid, argatroban, RWJ 445167, RWJ-671818, and mixtures thereof.

In a further embodiment of the invention, the biologically active agent is selected from the group consisting of antigens in the form of proteins, polysaccharides, oligosaccharides, lipoproteins, weakened or killed viruses such as cytomegalovirus, hepatitis B virus, hepatitis C virus, human papillomavirus, rubella virus, and *varicella zoster*, weakened or killed bacteria such as *bordetella pertussis, clostridium tetani, corynebacterium diphtheriae*, group A *streptococcus, legionella pneumophila, neisseria meningitides, pseudomonas aeruginosa, streptococcus pneumoniae, treponema pallidum*, and *vibrio cholerae* and mixtures thereof.

In another embodiment, the agent formulation includes at least one additional pharmaceutical agent selected from the group consisting of pathway patency modulators and vasoconstrictors.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Figure 1:
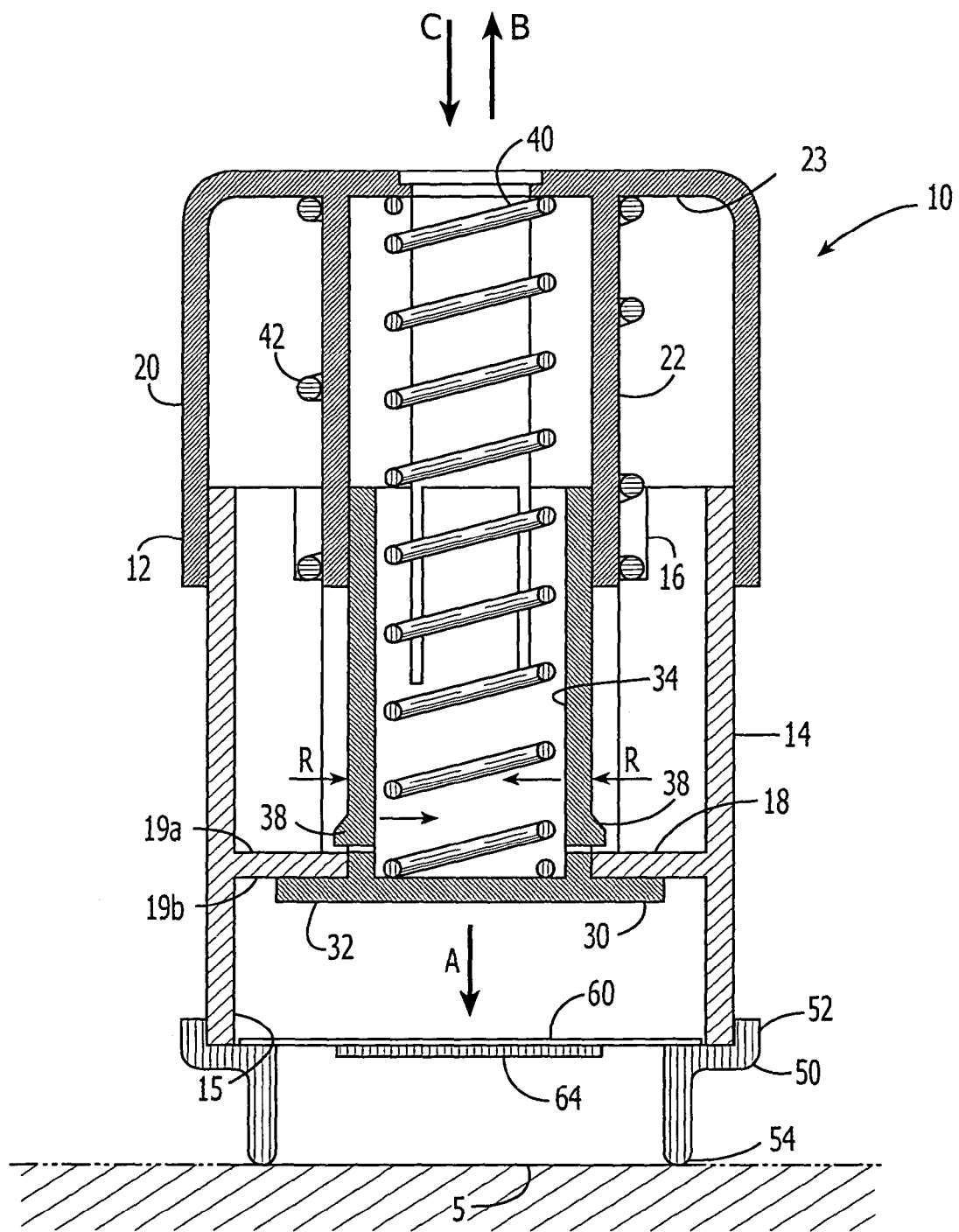
FIG. 1 is a front cross-sectional view of one embodiment of the applicator illustrating an initial configuration or primary position with a patch retainer attached to the applicator, according to the invention.

Before describing the present invention in detail, it is to be understood that this invention is not limited to particularly exemplified materials, methods or structures as such may, of course, vary. Thus, although a number of materials and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "a microprojection" includes two or more such microprojections and the like.

DEFINITIONS

The term "transdermal", as used herein, means the delivery of an agent into and/or through the skin for local or systemic therapy.

The term "transdermal flux", as used herein, means the rate of transdermal delivery.

The term "biologically active agent", as used herein, refers to a composition of matter or mixture containing a drug which is pharmacologically effective when administered in a therapeutically effective amount. Examples of such active agents include, without limitation, leutinizing hormone releasing hormone (LHRH), LHRH analogs (such as goserelin, leuprolide, buserelin, triptorelin, gonadorelin, and napfarelin, menotropins (urofollitropin (FSH) and LH)), vasopressin, desmopressin, corticotrophin (ACTH), ACTH analogs such as ACTH (1-24), calcitonin, vasopressin, deamino [Val4, D-Arg8] arginine vasopressin, interferon alpha, interferon beta, interferon gamma, erythropoietin (EPO), granulocyte macrophage colony stimulating factor (GM-CSF), granulocyte colony stimulating factor (G-CSF), interleukin-10 (IL-10), glucagon, growth hormone releasing factor (GHRF), insulin, insulinotropin, calcitonin, octreotide, endorphin, TRN, NT-36 (chemical name: N-[[(s)-4-oxo-2-azetidinyl]carbonyl]-L-histidyl-L-prolinamide), liprecin, aANF, bMSH, somatostatin, bradykinin, somatotropin, platelet-derived growth factor releasing factor, chymopapain, cholecystokinin, chorionic gonadotropin, epoprostenol (platelet aggregation inhibitor), glucagon, hirulog, interferons, interleukins, menotropins (urofollitropin (FSH) and LH), oxytocin, streptokinase, tissue plasminogen activator, urokinase, ANP, ANP clearance inhibitors, angiotensin II antagonists, antidiuretic hormone agonists, bradykinin antagonists, ceredase, CSI's, calcitonin gene related peptide (CGRP), enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vasopressin antagonists analogs, alpha-1 antitrypsin (recombinant), TGF-beta, fondaparinux, ardeparin, dalteparin, defibrotide, enoxaparin, hirudin, nadroparin, reviparin, tinzaparin, pentosan polysulfate, oligonucleotides and oligonucleotide derivatives, such as formivirsen, alendronic acid, clodronic acid, etidronic acid, ibandronic acid, incadronic acid, pamidronic acid, risedronic acid, tiludronic acid, zoledronic acid, argatroban, RWJ 445167, RWJ-671818, and mixtures thereof.

The noted biologically active agents can also be in various forms, such as free bases, acids, charged or uncharged molecules, components of molecular complexes or nonirritating, pharmacologically acceptable salts. Further, simple derivatives of the active agents (such as ethers, esters, amides, etc.), which are easily hydrolyzed at body pH, enzymes, etc., can be employed.

The term "biologically active agent", as used herein, also refers to a composition of matter or mixture containing a "vaccine" or other immunologically active agent or an agent which is capable of triggering the production of an immunologically active agent, and which is directly or indirectly immunologically effective when administered in an immunologically effective amount.

The term "vaccine", as used herein, refers to conventional and/or commercially available vaccines, including, but not limited to, flu vaccines, Lyme disease vaccine, rabies vaccine, measles vaccine, mumps vaccine, chicken pox vaccine, small pox vaccine, hepatitis vaccine, pertussis vaccine, and diphtheria vaccine, recombinant protein vaccines, DNA vaccines and therapeutic cancer vaccines. The term "vaccine" thus includes, without limitation, antigens in the form of proteins, polysaccharides, oligosaccharides, lipoproteins, weakened or killed viruses such as cytomegalovirus, hepatitis B virus, hepatitis C virus, human papillomavirus, rubella virus, and *varicella zoster*, weakened or killed bacteria such as *bordetella pertussis, clostridium tetani, corynebacterium diphtheriae*, group A *streptococcus, legionella pneumophila, neisseria meningitides, pseudomonas aeruginosa, streptococcus pneumoniae, treponema pallidum,* and *vibrio cholerae* and mixtures thereof.

It is to be understood that more than one biologically active agent can be incorporated into an agent formulation or microprojection microprojection coating of, and that the use of the term "active agent" in no way excludes the use of two or more such active agents.

The term "biologically effective amount" or "biologically effective rate" shall be used when the biologically active agent is a pharmaceutically active agent and refers to the amount or rate of the pharmacologically active agent needed to effect the desired therapeutic, often beneficial, result.

The term "biologically effective amount" or "biologically effective rate" shall also be used when the biologically active agent is an immunologically active agent and refers to the amount or rate of the immunologically active agent needed to stimulate or initiate the desired immunologic, often beneficial result.

The term "vasoconstrictor", as used herein, refers to a composition of matter or mixture that narrows the lumen of blood vessels and, hence, reduces peripheral blood flow. Examples of suitable vasoconstrictors include, without limitation, amidephrine, cafaminol, cyclopentamine, deoxyepinephrine, epinephrine, felypressin, indanazoline, metizoline, midodrine, naphazoline, nordefrin, octodrine, orinpressin, oxymetazoline, phenylephrine, phenylethanolamine, phenylpropanolamine, propylhexedrine, pseudoephedrine, tetrahydrozoline, tramazoline, tuaminoheptane, tymazoline, vasopressin, xylometazoline and the mixtures thereof.

The terms "microprojections" and "microprotrusions", as used herein, refer to piercing elements that are adapted to pierce or cut through the stratum corneum into the underlying epidermis layer, or epidermis and dermis layers, of the skin of a living animal, particularly a mammal and more particularly a human.

In one embodiment of the invention, the microprojections have a projection length less than 1000 microns. In a further embodiment, the microprojections have a projection length of less than 500 microns, more preferably, less than 250 microns. The microprojections typically have a width and thickness of about 5 to 50 microns. The microprojections may be formed in different shapes, such as needles, blades, pins, punches, and combinations thereof.

The term "microprojection array", as used herein, refers to a plurality of microprojections arranged in an array for piercing the stratum corneum. The microprojection array may be formed by etching or punching a plurality of microprojections from a thin sheet and folding or bending the microprojections out of the plane of the sheet to form a configuration, such as that shown in FIG. 5. The microprojection array may also be formed in other known manners, such as by forming one or more strips having microprojections along an edge of each of the strip(s) as disclosed in U.S. Pat. No. 6,050,988.

References to the area of the sheet or member and reference to some property per area of the sheet or member are referring to the area bounded by the outer circumference or border of the sheet.

As will be appreciated by one having ordinary skill in the art, the applicator of the present invention can be readily employed for repeatable impact application of an array of microprojections to the stratum corneum in conjunction with transdermal therapeutic agent delivery or sampling. Although the applicator 10 is described for use with a certain type of microprojection array, it should be understood that the applicator can also be used with other types of stratum corneum micro-penetrating members.

As discussed in detail herein, the applicator of the invention is auto pre-setting and thus eliminates the step of manually pre-setting the applicator prior to use. The applicator is also auto-triggering. The applicator can thus be readily used by patients having neither the hand strength, nor the manual dexterity to pre-set other types of spring-loaded applicator devices.

The applicator of the invention additionally employs a triggering mechanism that is loaded outside of the diameter of the impact spring that biases the piston away from the device, allowing the use of smaller diameter springs made from smaller diameter wire, which can store equal or greater energy with the same travel while weighing less. The reduced mass of the impact spring also permits a lower force to be used to compress the spring in order to achieve greater impact velocity.

Further, the impact spring and the pre-setting spring have different inner and outer diameters and their positions in the applicator prevent the possibility of accidentally placing a spring in the wrong location. The piston, inner cup and outer cup can also be keyed so they can only be assembled in a functional orientation.

The piston, inner cup and outer cup are also designed and configured to snap together to avoid the need for additional assembly steps, such as inserting screws, ultrasonic welding, adhesive bonding or solvent bonding. The snaps also make disassembly of the applicator difficult, discouraging anyone from tampering with the mechanism.

Figure 2:
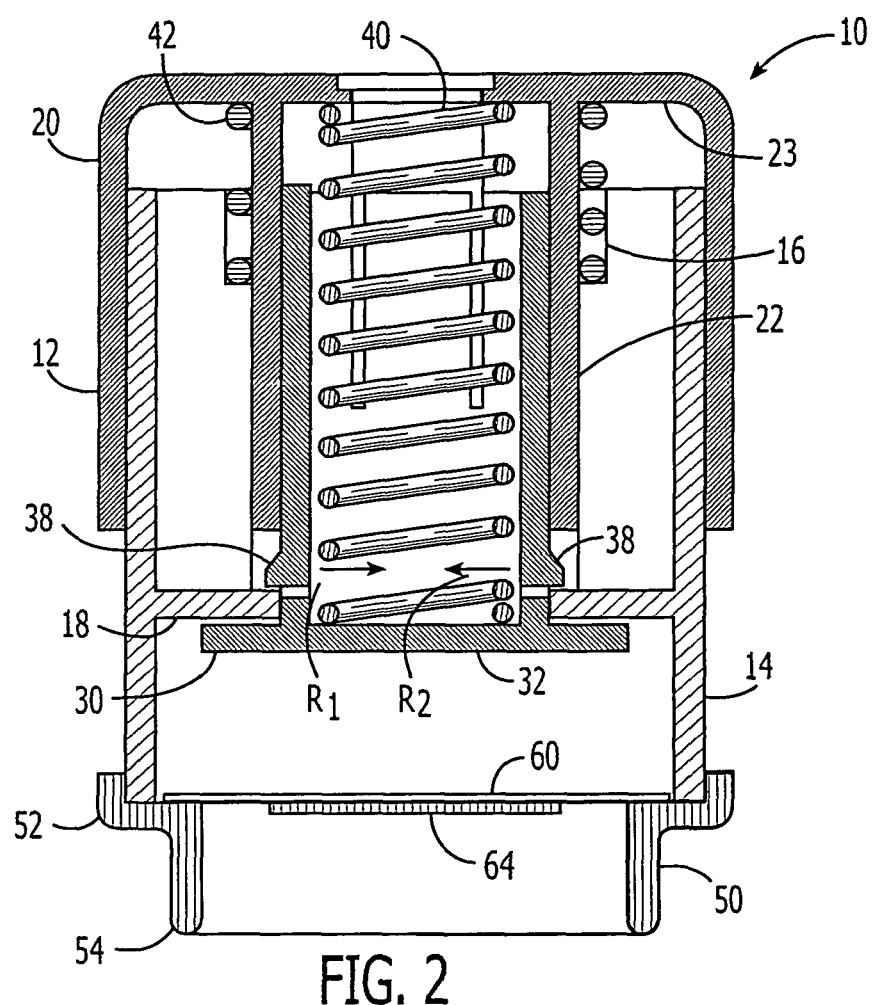
FIG. 2 is a front cross-sectional view of the retainer illustrating a pre-set position, according to the invention.
Figure 3:
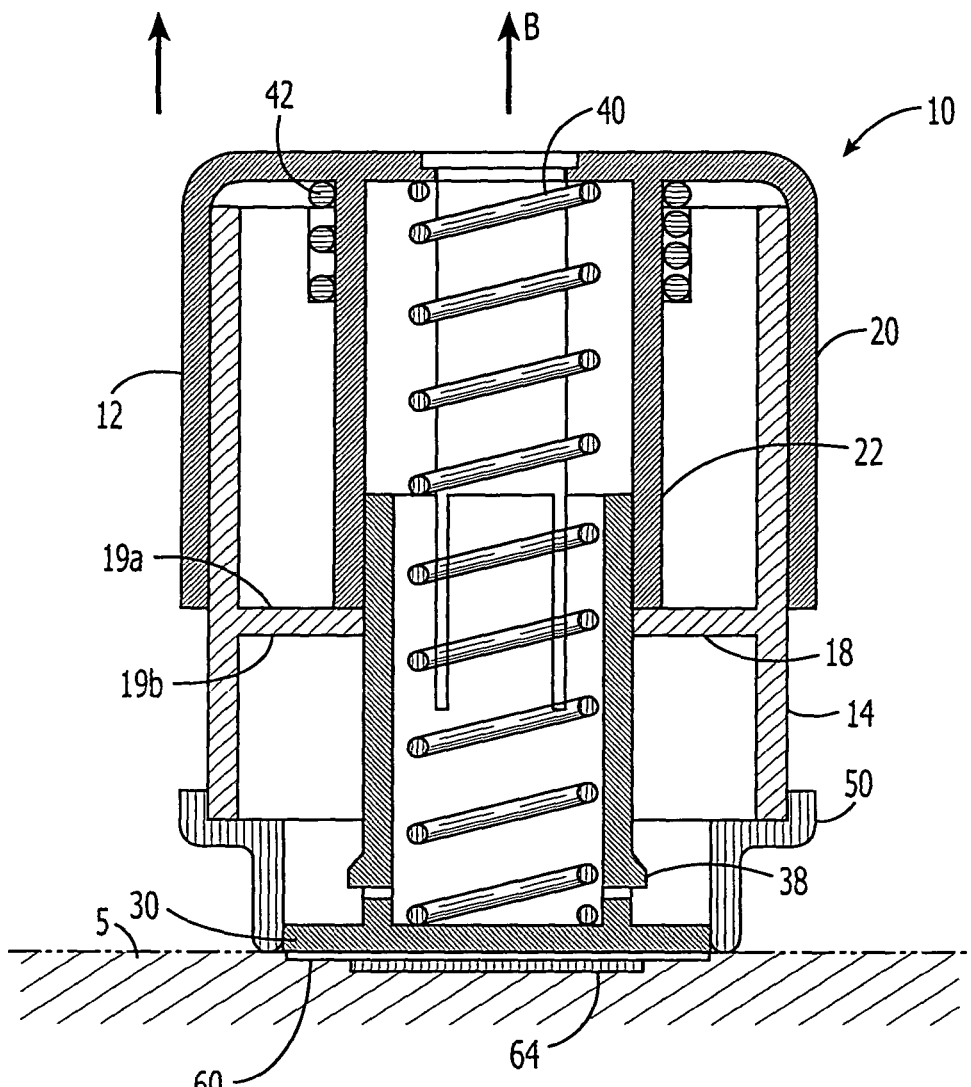
FIG. 3 is a front cross-sectional view of the retainer illustrating a an activated position with the piston proximate a skin site, according to the invention.

Referring now to FIGS. 1-3, the applicator 10 generally includes a housing 12, having an inner cup 14, and a piston 30 movable within the housing 12. As illustrated in FIG. 1, the housing 12 further includes an outer cup (or cap) 20 for actuating the applicator 10 to impact the stratum corneum with a patch 60 or microprojection array 64.

The applicator 10 further includes an impact spring 40 that is positioned inside the spring guide 22 that extends inwardly from the top 23 of the outer cup 20. The impact spring 40 is also seated in the piston spring seat or recess 34.

According to the invention, the impact spring 40 biases the piston 30 downward (in the direction denoted by arrow A) with respect to the applicator housing 12.

As illustrated in FIG. 2, the piston 30 has a lower surface or face 32, which, according to the invention, can be substantially planar, slightly convex or configured to a body surface (i.e., a specific skin site). As discussed in detail herein, when the applicator 10 is actuated, the lower surface 32 of the piston 30 causes a microprojection array or a transdermal patch containing a microprojection array to impact and pierce the stratum corneum.

According to the invention, the piston face 32 preferably has a surface area in the range of approximately 0.1-20 cm². More preferably, the piston face 32 has a surface area in the range of approximately 1-10 cm².

Referring back to FIG. 1, the applicator 10 additionally includes a pre-setting spring 42 that is positioned around the impact spring. The pre-setting spring 42 is also seated in the spring seat 16 disposed proximate the top of the inner cup 14. As discussed in detail herein, the pre-setting spring 42 biases the outer cup 20 upward (in the direction denoted by arrow B) with respect to the inner cup 14 after actuation of the applicator 10.

As illustrated in FIG. 1, the inner cup 14 further includes a piston stop 18, having a top 19*a* and bottom 19*b* surface that maintains the piston 30 in a pre-set position and restricts motion of the piston 30 there beyond in an upward direction.

Figure 4:
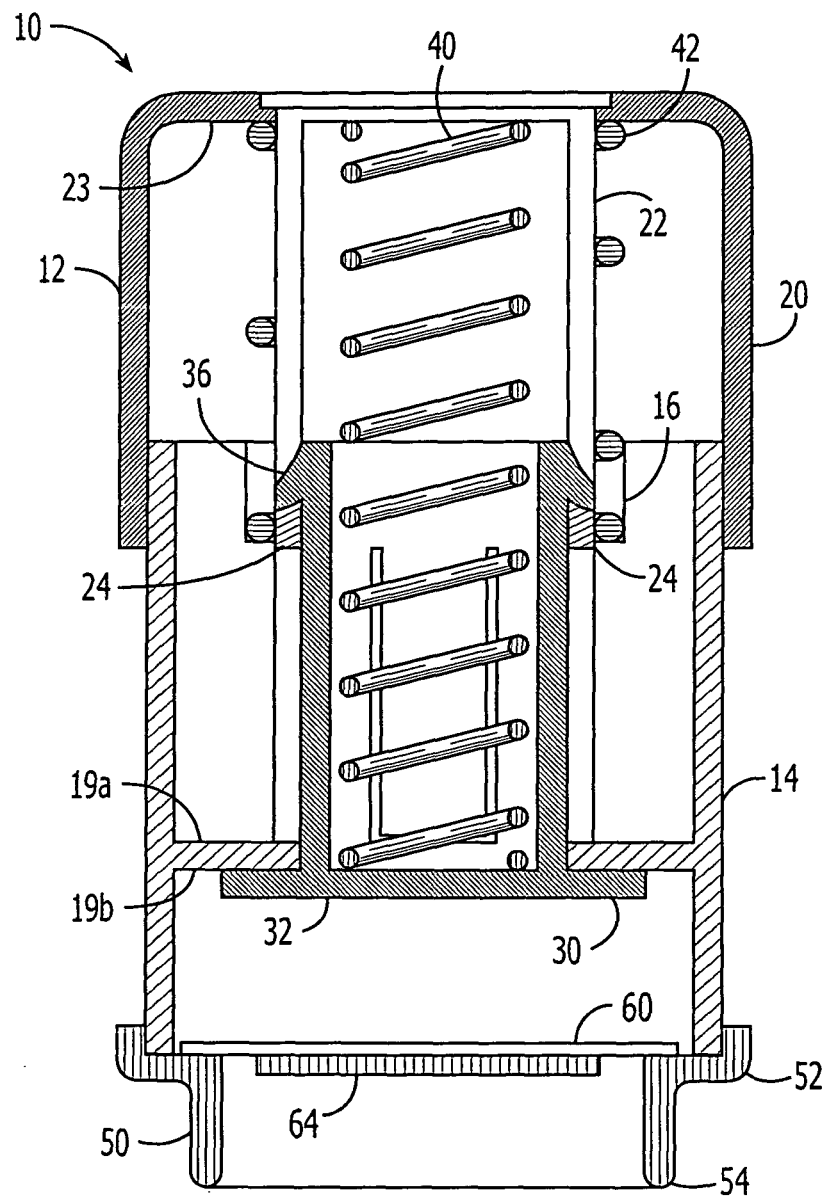
FIG. 4 is a side cross-sectional view of the applicator in the primary position shown in FIG. 1.

Referring now to FIG. 4 (which is a further sectional view of the applicator 10 rotated approximately 90° with respect to the view shown in FIG. 1) the piston 30 includes at least one, more preferably, at least two, locking members 36 (i.e., first latching assembly) that are disposed proximate the end opposite the piston face 32. According to the invention, the locking members 36 are adapted to contact the outer cup 20 locking member seat 24 after actuation of the applicator 10 (see FIG. 6) and raise the piston 30 to pre-set position, as illustrated in FIG. 4.

As illustrated in FIG. 1, the piston 30 further includes at least one, more preferably, at least two, flexible release catches 38 (i.e., second latching assembly). According to the invention, the release catches 38 are designed and adapted to communicate with (or be positioned on) the top 19*a* of the inner cup 14 piston stop 18. (see FIGS. 1 and 2). As discussed in detail below, the release catches 38 are further adapted to flex inwardly and, hence, disengage from the stop 18 when the cup 20 and, hence, spring guide 22 moves from the primary position to the pre-set position (see FIG. 2).

Figure 7:
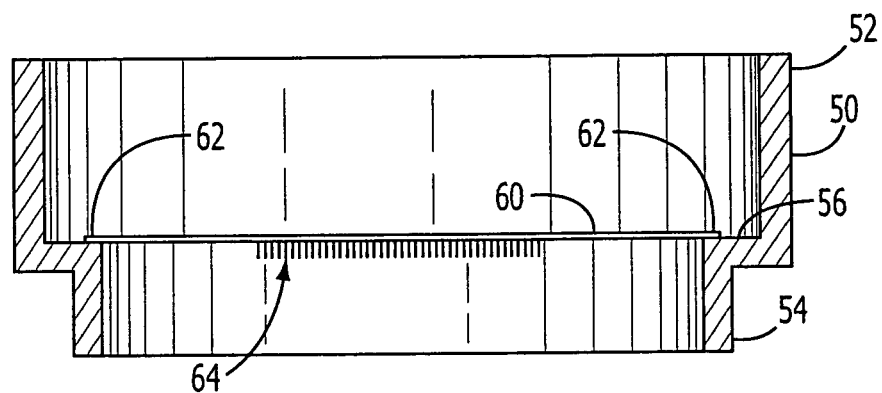
FIG. 7 is a front cross-sectional view of a patch retainer that is adapted to cooperate with the applicator shown in FIGS. 1 through 6, according to the invention.
Figure 8:
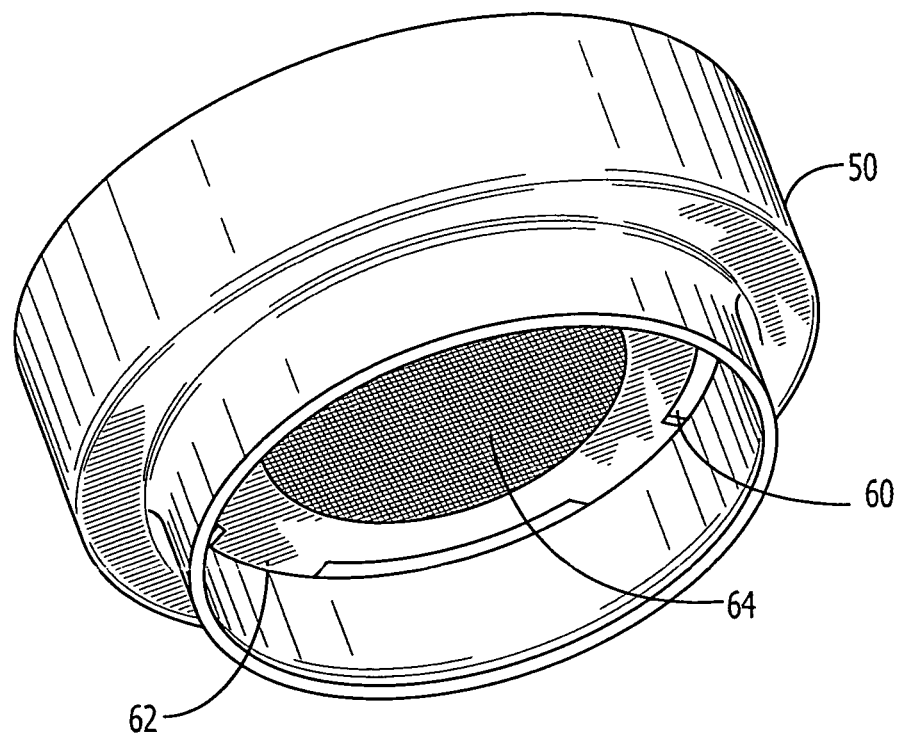
FIG. 8 is a perspective view of the patch retainer shown in FIG. 7.

FIGS. 1-6 further illustrate a patch retainer 50 operatively secured to the applicator 10. Referring now to FIGS. 7 and 8, the retainer 50 preferably has a substantially annular shape with a first end 52 that is configured to engage the leading end 15 of the inner cup 14. The second or leading end 54 of the retainer 50 provides a stratum corneum contacting surface.

Referring now to FIG. 7, the retainer 50 includes a patch seat 56 that is adapted to receive the patch 60. Although the manner in which the patch 60 is mounted in the retainer 50 can vary (for example, the patch 60 may be positioned proximate the leading end 54 of the retainer 50), it is preferred that the patch 60 is mounted distal from the leading end 54, as illustrated in FIG. 8, in order to avoid inadvertent contact of the patch microprojections with other objects (e.g., the fingers of the user).

According to one example, the patch 60 is connected by frangible sections of patch base material to an annular ring of patch material 62, which is adhered to the patch seat 56. The patch 60 is separated from the retainer seat 56 by the downward force of the piston 30. Alternatively, patch 60 may be releasably attached to the piston 30 or positioned on the skin beneath the piston 30.

As indicated, two significant features of the applicator 10 are the locations of the impact spring 40 and pre-setting spring 42, and the use of a small diameter and, hence, low mass impact spring 40.

As is well known in the art, the mass (m) of a spring is a function of the density of the spring material ($\rho$), the diameter of the wire (d) and the length of the wire (L);

$$m = \rho \pi L d^2 / 4$$

the length of the wire (L) being a function of the mean diameter of the spring (D), the length of the spring (s) and the pitch (P):

$$L = \frac{s\sqrt{(\pi D)^2 + P^2}}{P}$$

As is further well known in the art, the stiffness of the spring (k) is a function of the modulus of the spring material (E), the diameter of the wire (d), the mean diameter of the spring (D), the length of the spring (s) and the pitch (P):

$$k = EPd^4 / 8sD^3$$

In order to maximize the stiffness-to-weight ratio of the impact spring, the diameter of the wire, d, should be maximized and the mean diameter of the spring should be minimized.

Further, the energy stored in the spring (PE) is a function of the stiffness of the spring (k) and the amount of compression in the spring at the start ($x_0$) and end ($x_1$) of its travel:

$$PE = k(x_1^2 - x_0^2)/2$$

In accordance with the noted relationships and one embodiment of the invention, the impact spring 40 has a stored or impact energy in the range of approximately 0.005-0.5 joules/cm², wherein the area (i.e., cm²) refers to the piston face 32. More preferably, the impact spring 40 has a stored energy in the range of approximately 0.01-0.3 joules/cm².

According to the invention, in the illustrated embodiment, the impact spring 40 has an impact velocity in the range of 0.5-20 m/sec. More preferably, the impact spring 40 has a velocity in the range of 1-10 m/sec.

Referring now to the figures, the operation of the applicator 10 will be described in detail. Referring first to FIGS. 1 and 4, there is shown the applicator 10 in a primary or ready position with the patch 60 positioned in the retainer 50. As illustrated in FIG. 1, in the primary position, the piston 30 is positioned against the piston stop 18 and the flexible release catches 38 are seated on the top 19*a* of the piston stop 18.

Figure 6:
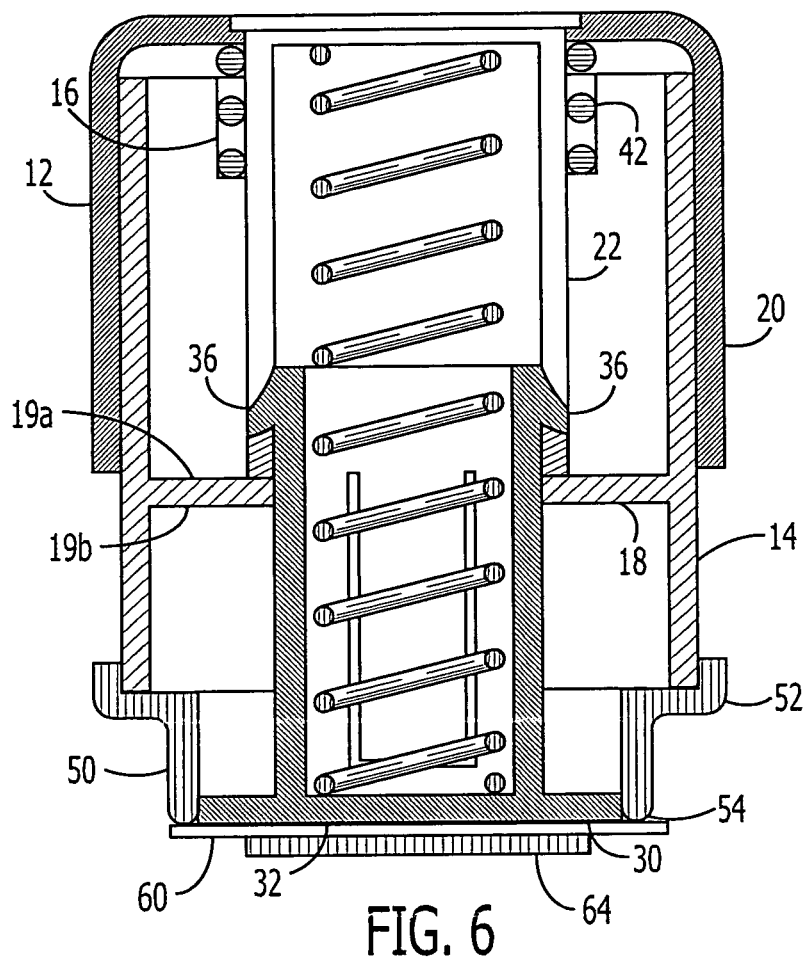
FIG. 6 is a side cross-sectional view of the applicator in the activated position shown in FIG. 3.

Referring now to FIG. 2 and FIG. 4 (which is a further cross-sectional view of the applicator 10 rotated approximately 90° with respect to the view shown in FIG. 2), when a user places the applicator 10 against a skin site 5 and exerts a downward force on the outer cup 20 (in a direction denoted by arrow B), the impact 40 and pre-setting 42 springs compress (i.e., energize) until the spring guide 22 contacts the release catches 38, flexing the release catches 38 inward (in the direction denoted by arrow $R_1$ and $R_2$) whereby the release catches 38 disengage from the piston stop 18 and the piston 30 moves downward to an activated position and impacts the skin site 5 (i.e., stratum corneum) with the patch 60 (see FIGS. 3 and 6).

According to the invention, the force exerted on the cap 20 and, hence, skin site 5 (i.e., hold-down force) prior to the noted activation is preferably less than 15 lbs., more preferably, the hold-down force is in the range of approximately 2-15 lbs. Even more preferably, the hold-down force is in the range of approximately 5-10 lbs., which substantially reduces and, in most instances, eliminates re-coil of the applicator 10.

According to the invention, the hold-down force causes the stratum corneum to be stretched by the leading end 54 of the retainer 50 so that the skin site 5 is under optimal tension at the time the patch 60 impacts the skin site 5. In a further envisioned embodiment of the invention (not shown), the retainer 50 includes a flexible biasing ring that is disposed on the leading end 54 of the retainer 50 that further stretches the stratum corneum when the releasing force is applied to the applicator 10.

Referring now to FIGS. 3 and 6, when the piston 30 is in the activated position (wherein the piston 30 is proximate the leading end 54 of the retainer 50), the pre-setting spring 42 is compressed (or energized) and, hence, biases the applicator outer cup 20 in an upward direction. The biasing force provided by the pre-setting spring 42 moves the outer cup 20 and piston 30, which is in communication therewith (see FIG. 6), back to the primary position illustrated in FIGS. 1 and 6 when the downward force is removed from the outer cup 20.

In a further envisioned embodiment, not shown, the release catches 38 have a sloping face that communicates with the top 19a of the piston stop 18. According to this embodiment, when a user places the applicator against a skin site 5 and exerts a downward force, the impact 40 and pre-setting 42 springs compress and energize until a releasing force is achieved, whereby the release catches 38 disengage (i.e., slide off the piston stop 18) and the piston 30 moves downward to the activated position shown in FIGS. 3 and 6.

The applicator 10 of the invention can be used with a patch 60 that generally includes a microprojection array 64, an agent reservoir, and a backing. However, the applicator 10 can also be used with a microprojection array without an agent reservoir. In this case, the microprojection array is used as a pretreatment member, which is followed by the application of an agent with a separate transdermal agent delivery or sampling device, such as disclosed in Co-Pending U.S. application Ser. No. 60/514,387, which is incorporated by reference herein in its entirety.

Alternatively, the microprojection array may incorporate the agent as a coating on the microprojections, e.g., for delivering a vaccine intradermally, such as disclosed in U.S. application Ser. Nos. 10/674,626 and 60/514,433, which are incorporated by reference herein in their entirety. U.S. application Ser. No. 10/674,626 discloses skin piercing microprojections having a dry coating of the biologically active agent and a vasoconstrictor.

The applicator 10 can also be used for impacting other micro-piercing elements against the stratum corneum, for example those disclosed in U.S. Pat. No. 5,879,326 and PCT Pub. WO 99/29364, which are similarly incorporated by reference herein in their entirety.

Figure 5:
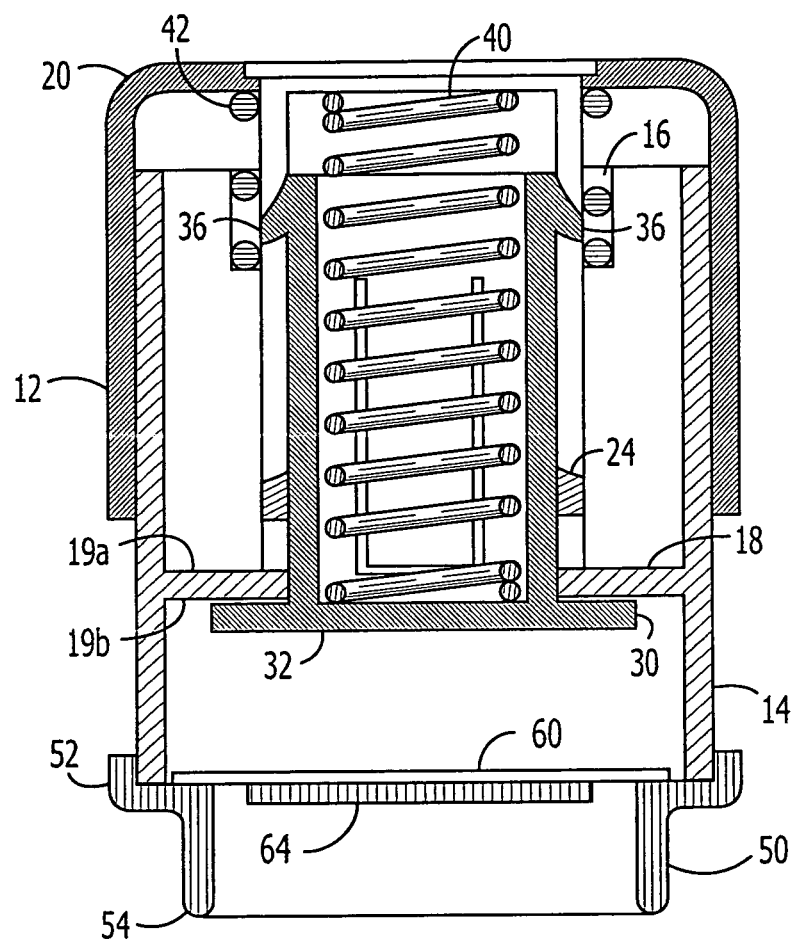
FIG. 5 is a side cross-sectional view of the applicator in the pre-set position shown in FIG. 2.
Figure 9:
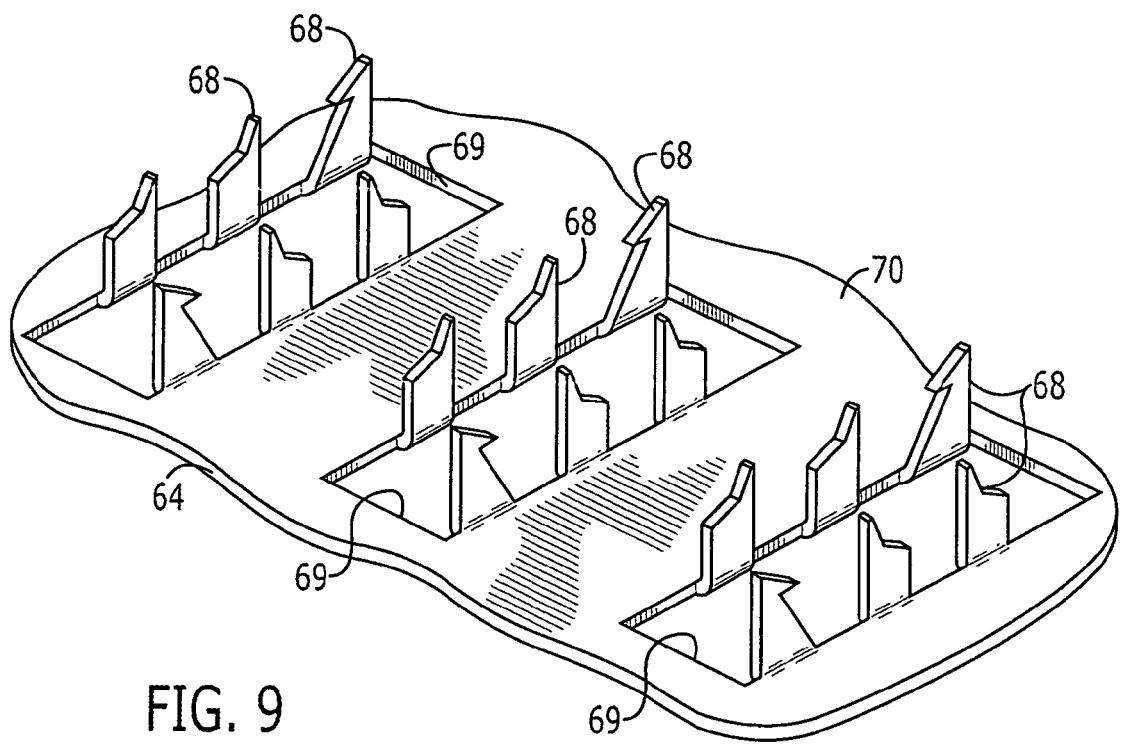
FIG. 9 is a partial perspective view of one embodiment of a microprojection array.

Referring now to FIG. 9 there is shown one embodiment of a microprojection array 64 that can be employed within the scope of the present invention. As illustrated in FIG. 5, the microprojection array 64 includes a plurality of microprojections 68 that extend downward from one surface of a sheet or plate 70. The microprojections 68 are preferably sized and shaped to penetrate the stratum corneum of the epidermis when pressure is applied to the array 64 (or patch 60).

The microprojections 68 are further adapted to form microslits in a body surface to increase the administration of a substance (e.g., hydrogel formulation) through the body surface. The term "body surface", as used herein, refers generally to the skin of an animal or human.

The microprojections 68 are generally formed from a single piece of sheet material and are sufficiently sharp and long to puncture the stratum corneum of the skin.

In the illustrated embodiment, the sheet 70 is formed with an opening 69 between the microprojections 68 to enhance the movement of the active agent therethrough.

Further details of the microprojection array 64 described above and other microprojection devices and arrays that can be employed within the scope of the invention are disclosed in U.S. Pat. Nos. 6,322,808, 6,230,051 B1 and Co-Pending U.S. application Ser. No. 10/045,842, which are incorporated by reference herein in their entirety.

As will be appreciated by one having ordinary skill in the art, the applicator of the present invention can be used in connection with transdermal agent delivery, transdermal analyte (e.g., glucose) sampling, or both. Transdermal delivery devices for use with the present invention include, but are not limited to, passive devices, negative pressure driven devices, osmotic devices, and reverse electrotransport devices.

From the foregoing description, one of ordinary skill in the art can easily ascertain that the present invention, among other things, provides an effective and efficient means for delivering biologically active agents to a patient.

As will be appreciated by one having ordinary skill in the art, the present invention provides many advantages, such as:

Self-setting

Auto-triggering

Lower hold-down or releasing force compared to prior art applicators

Easy assembly

Virtually tamper resistant

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A device for impacting a microprojection member against the stratum corneum of a patient, comprising:

a housing;

a piston moveable within the housing;

a cap adapted to activate the piston so the piston is capable of impacting the microprojection member against the stratum corneum of a patient; the device being one-handed self-setting and auto-triggering;

an impact spring in communication with the cap and the piston, the impact spring being adapted to provide an impact force to the piston and bias the piston to an activated position, wherein the impact spring is energized when the cap and the piston are in a pre-set position;

a pre-setting spring in communication with the cap and the housing, said pre-setting spring being adapted to provide a pre-setting force to the cap and bias the cap from the pre-set position to a primary position, wherein the pre-setting spring is energized when the piston is in said activated position;
a first latching assembly in communication with the cap and the piston, said first latching assembly being adapted to cooperate with the cap and the pre-setting spring to return the piston to the primary position when the cap is moved from the pre-set position to the primary position;
wherein said pre-setting spring is positioned around said impact spring, and
wherein said pre-setting spring is not in communication with said piston, and
wherein the microprojection member comprises a plurality of stratum corneum piercing blades having a dry coating disposed thereon, and wherein the coating includes at least one biologically active agent consisting of parathyroid hormone (PTH).

2. The device of claim 1, wherein said impact spring has a stored energy in the range of approximately 0.005-0.5 joules/$cm^2$.

3. The device of claim 2, wherein said impact spring has a stored energy in the range of approximately 0.01-0.3 joules/$cm^2$.

4. The device of claim 1, wherein said impact spring has an impact velocity in the range of approximately 0.5-20 m/sec.

5. The device of claim 4, wherein said impact spring has an impact velocity in the range of approximately 1.0-10 m/sec.

6. The device of claim 1, wherein said piston includes a face, said face having a surface area in the range of approximately 0.1-20 $cm^2$.

7. The device of claim 6, wherein said face has a surface area in the range of approximately 1.0-10 $cm^2$.

8. The device of claim 1, wherein the coating includes an agent formulation having at least one biologically active agent.

9. The device of claim 1, wherein the cap is adapted to move from a said primary position to a said pre-set position relative to the housing and the piston is adapted to move from the pre-set position to an activated position.

10. The device of claim 1, wherein the device does not contain a physical reservoir separate from the dry coating.

11. The device of claim 1, further comprising a second latching assembly in communication with the housing and the piston to position the piston in the pre-set position.

12. The device of claim 11, further comprising a releasing member in communication with the cap, said releasing member being adapted to communicate with the second latching assembly when the cap is moved from the primary position to the pre-set position, wherein the impact spring is energized and the releasing member disengages, whereby the piston moves from the pre-set position to the activated position and forces the microprojection member into the stratum corneum.

13. A device for impacting a microprojection member against the stratum corneum of a patient, comprising:

a housing;

a piston moveable within the housing; and a cap adapted to activate the piston so the piston is capable of impacting the microprojection member against the stratum corneum of a patient;

the device being one-handed self-setting and auto-triggering:

wherein the cap is adapted to move from a primary position to a pre-set position relative to the housing and the piston is adapted to move from the pre-set position to an activated position;

an impact spring in communication with the cap and the piston, the impact spring being adapted to provide an impact force to the piston and bias the piston to an activated position, wherein the impact spring is energized when the cap and the piston are in the pre-set position;

a pre-setting spring in communication with the cap and the housing, said pre-setting spring being adapted to provide a pre-setting force to the cap and bias the cap from the pre-set position to the primary position;

a first latching assembly in communication with the cap and the piston, said first latching assembly being adapted to cooperate with the cap and the pre-setting spring to return the piston to the primary position when the cap is moved from the pre-set position to the primary position;

wherein said pre-setting spring is positioned around said impact spring, and wherein said pre-setting spring is not in communication with said piston, and wherein the pre-setting spring is energized when the piston is in said activated position, and wherein the microprojection member comprises a plurality of stratum corneum piercing blades having a dry coating disposed thereon, and wherein the coating includes at least one biologically active agent consisting of parathyroid hormone (PTH).

14. The device of claim 13, wherein said coating includes at least one pathway patency modulator.

15. The device of claim 13, wherein said coating includes at least one vasoconstrictor.

16. The device of claim 13, wherein the device does not contain a physical reservoir separate from the dry coating.

17. The device of claim 13, further comprising a second latching assembly in communication with the housing and the piston to position the piston in the pre-set position.

18. The device of claim 17, further comprising a releasing member in communication with the cap, said releasing member being adapted to communicate with the second latching assembly when the cap is moved from the primary position to the pre-set position, wherein the impact spring is energized and the releasing member disengages, whereby the piston moves from the pre-set position to the activated position and forces the microprojection member into the stratum corneum.

19. A device for impacting a microprojection member against the stratum corneum of a patient, comprising:

a housing;

a piston moveable within the housing; and a cap adapted to activate the piston so the piston is capable of impacting the microprojection member against the stratum corneum of a patient;

the device being one-handed self-setting and auto-triggering:

wherein the cap is adapted to move from a primary position to a pre-set position relative to the housing and the piston is adapted to move from the pre-set position to an activated position;

an impact spring in communication with the cap and the piston, the impact spring being adapted to provide an impact force to the piston and bias the piston to an activated position, wherein the impact spring is energized when the cap and the piston are in the pre-set position;

a pre-setting spring in communication with the cap and the housing, said pre-setting spring being adapted to provide a pre-setting force to the cap and bias the cap from the pre-set position to the primary position;

a first latching assembly in communication with the cap and the piston, said first latching assembly being adapted to cooperate with the cap and the pre-setting spring to return the piston to the primary position when the cap is moved from the pre-set position to the primary position;

wherein said pre-setting spring is positioned around said impact spring, and wherein said pre-setting spring is not in communication with said piston, and wherein the pre-setting spring is energized when the piston is in said activated position, and wherein the microprojection member comprises a plurality of stratum corneum piercing blades having a dry coating disposed thereon, wherein said biologically active agent is selected from the group consisting of a leutinizing hormone releasing hormone (LHRH), LHRH analogs, vasopressin, desmopressin, corticotropin (ACTH), ACTH analogs, calcitonin, vasopressin, deamino [Val4, D-Arg8] arginine vasopressin, interferon alpha, interferon beta, interferon gamma, erythropoietin (EPO), granulocyte macrophage colony stimulating factor (GM-CSF), granulocyte colony stimulating factor (G-CSF), interleukin-10 (IL-10), glucagon, growth hormone release hormone (GHRH), growth hormone release factor (GHRF), insulin, insultropin, calcitonin, octreotide, endorphin, TRN, N-[[(s)-4-oxo-2-azetidinyl]carbonyl]-L-histidyl-L-prolinamide, liprecin, pituitary hormones, follicle luteoids, aANF, growth factors, bMSH, GH, somatostatin, bradykinin, somatotropin, platelet-derived growth factor releasing factor, asparaginase, bleomycin sulfate, chymopapain, cholecystokinin, chorionic gonadotropin, corticotropin (ACTH), erythropoietin, epoprostenol (platelet aggregation inhibitor), glucagon, HCG, hirulog, hyaluronidase, interferon, interleukins, menotropins (urofollitropin (FSH) and LH), oxytocin, streptokinase, tissue plasminogen activator, urokinase, vasopressin, desmopressin, ANP, ANP clearance inhibitors, angiotensin II antagonists, antidiuretic hormone agonists, bradykinn antagonists, ceredase, CSI's, calcitonin gene related peptide (CGRP), enkephalins, FAB fragments, IgE peptide suppressors, IGF-1, neurotrophic factors, colony stimulating factors, parathyroid hormone antagonists, prostaglandin antagonists, pentigetide, protein C, protein S, renin inhibitors, thymosin alpha-1, thrombolytics, TNF, vasopressin antagonists analogs, alpha-1 antitrypsin (recombinant), TGF-beta, fondaparinux, ardeparin, dalteparin, defibrotide, enoxaparin, hirudin, nadroparin, reviparin, tinzaparin, pentosan polysulfate, oligonucleotides and oligonucleotide derivatives, alendronic acid, clodronic acid, etidronic acid, ibandronic acid, incadronic acid, pamidronic acid, risedronic acid, tiludronic acid, zoledronic acid, argatroban, RWJ 445167, RWJ-671818, antigens in the form of proteins, polysaccharides, oligosaccharides, lipoproteins, weakened or killed viruses such as cytomegalovirus, hepatitis B virus, hepatitis C virus, human papillomavirus, rubella virus, and varicella zoster, weakened or killed bacteria such as *bordetella pertussis, clostridium tetani, corynebacterium diphtherias*, group A *streptococcus, legionella pneumophila, neisseria meningitides, pseudomonas aeruginosa, streptococcus pneumoniae, treponema pallidum*, and *vibrio cholerae* and mixtures thereof.

20. The device of claim 19, wherein the device does not contain a physical reservoir separate from the dry coating.

21. The device of claim 19, further comprising a second latching assembly in communication with the housing and the piston to position the piston in the pre-set position.

22. The device of claim 21, further comprising a releasing member in communication with the cap, said releasing member being adapted to communicate with the second latching assembly when the cap is moved from the primary position to the pre-set position, wherein the impact spring is energized and the releasing member disengages, whereby the piston moves from the pre-set position to the activated position and forces the microprojection member into the stratum corneum.

* * * * *